United States Patent [19]
Müller et al.

[11] Patent Number: 6,001,776
[45] Date of Patent: Dec. 14, 1999

[54] HERBICIDAL SULPHONYLAMINO(THIO) CARBONYL TRIAZOLIN(THI)ONES WITH HETEROCYCLYL(ALK)OXY SUBSTITUENTS

[75] Inventors: Klaus-Helmut Müller, Düsseldorf; Joachim Kluth, Langenfeld; Rolf Kirsten, Monheim; Ernst Rudolf Gesing, Erkrath; Kurt Findeisen, Leverkusen; Johannes Rudolf Jansen, Monheim; Klaus König, Odenthal; Mark Wilhelm Drewes, Langenfeld; Markus Dollinger; Hans-Joachim Santel, both of Leverkusen, all of Germany

[73] Assignee: Bayer Aktiengesellschaft, Leverkusen, Germany

[21] Appl. No.: 08/981,972

[22] PCT Filed: Jul. 4, 1996

[86] PCT No.: PCT/EP96/02933

§ 371 Date: Jan. 9, 1998

§ 102(e) Date: Jan. 9, 1998

[87] PCT Pub. No.: WO97/03981

PCT Pub. Date: Feb. 6, 1997

[30] Foreign Application Priority Data

Jul. 17, 1995 [DE] Germany .................. 195 25 973

[51] Int. Cl.⁶ .................................................. C07D 249/12
[52] U.S. Cl. ........................................ 504/273; 548/263.4
[58] Field of Search .................... 504/273; 548/263.4

[56] References Cited

U.S. PATENT DOCUMENTS 5,057,144 10/1991 Daum et al. .................................. 71/92
5,534,486 7/1996 Müller et al. .

FOREIGN PATENT DOCUMENTS 0 185 401 A1 6/1986 European Pat. Off. .
0 507 171 A1 10/1992 European Pat. Off. .

OTHER PUBLICATIONS

Cram and Hammond, "Organic Chemistry", McGraw–Hill Book Co., NY (1964) 2nd Ed, pp. 565–567.
Chemische Berichte, vol. 110, No. 5, 1977, pp. 1716–1729 (in German with English Abstract).

*Primary Examiner*—Patricia L. Morris
*Attorney, Agent, or Firm*—Sprung Kramer Schaefer & Briscoe

[57] ABSTRACT

The novel title compounds of the formula (I)

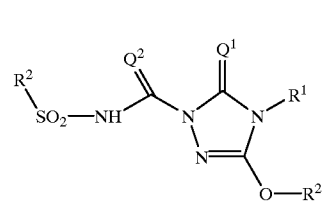

in which $Q^1$ represents oxygen or sulphur, $Q^2$ represents oxygen or sulphur, $R^1$ represents hydrogen, hydroxyl, amino or alkylideneamino or represents an in each case optionally substituted radical from the series consisting of alkyl, alkenyl, alkinyl, alkoxy, alkenyloxy, alkylamino, dialkylamino, alkanoylamino, cycloalkyl, cycloalkylalkyl, cycloalkylamino, aryl and arylalkyl, $R^2$ represents in each case optionally substituted heterocyclyl or heterocyclylalkyl, and $R^3$ represents an in each case optionally substituted radical from the series consisting of alkyl, aralkyl, aryl and heteroaryl, and salts of compounds of the formula (I), processes and novel intermediates for their preparation, and their use as herbicides.

5 Claims, No Drawings

HERBICIDAL SULPHONYLAMINO(THIO) CARBONYL TRIAZOLIN(THI)ONES WITH HETEROCYCLYL(ALK)OXY SUBSTITUENTS

This application is a 371 of PCT/EP96/02933 filed Jul. 4, 1996.

The invention relates to novel sulphonylamino(thio)carbonyltriazolin(thi)ones having heterocyclyl(alk)oxy substituents, to a number of processes and to novel intermediates for their preparation, and to their use as herbicides.

It is already known that certain sulphonylaminocarbonyltriazolinones possess herbicidal properties (cf. EP-341 489, EP-A 422 469, EP-A 425 948, EP-A 431 291, EP-A 507 171). The action of these compounds, however, is not in every respect satisfactory.

The novel sulphonylamino(thio)carbonyltriazolin(thi)ones having heterocyclyl(alk)oxy substituents have now been found of the general formula (I)

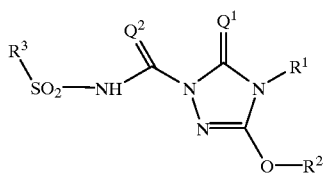

(I)

in which
- $Q^1$ represents oxygen or sulphur,
- $Q^2$ represents oxygen or sulphur,
- $R^1$ represents hydrogen, hydroxyl, amino or alkylideneamino or represents an in each case optionally substituted radical from the series consisting of alkyl, alkenyl, alkinyl, alkoxy, alkenytoxy, alkylamino, dialkylamino, alkanoylamino, cycloalkyl, cycloalkylalkyl, cycloalkylamino, aryl and arylalkyl,
- $R^2$ represents in each case optionally substituted heterocyclyl or heterocyclylalkyl, and
- $R^3$ represents an in each case optionally substituted radical from the series consisting of alkyl, aralkyl, aryl and heteroaryl, and salts of compounds of the formula (I).

The novel sulphonylamino(thio)carbonyltriazolin(thi)ones having heterocyclyl(alk)oxy substituents, of the general formula (I), are obtained if (a) triazolin(thi)ones of the general formula (II)

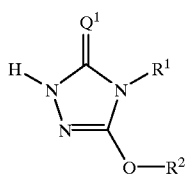

(II)

in which
$Q^1$, $R^1$ and $R^2$ have the meanings given above are reacted with sulphonyl iso(thio)cyanates of the general formula (III)

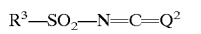

$$R^3\text{—}SO_2\text{—}N\text{=}C\text{=}Q^2 \qquad (III)$$

in which $Q^2$ and $R^3$ have the meanings given above, optionally in the presence of a reaction auxiliary and optionally in the presence of a diluent, or if (b) triazolin(thi)one derivatives of the general formula (IV)

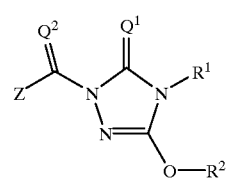

(IV)

in which
- $Q^1$, $Q^2$, $R^1$ and $R^2$ have the meanings given above and
- Z represents halogen, alkoxy, aralkoxy or aryloxy are reacted with sulphonamides of the general formula (V)

$$R^3\text{—}SO_2\text{—}NH_2 \qquad (V)$$

in which
$R^3$ has the meaning given above, optionally in the presence of an acid acceptor and optionally in the presence of a diluent,
or if (c) triazolin(thi)ones of the general formula (II)

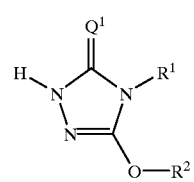

(II)

in which
$Q^1$, $R^1$ and $R^2$ have the meanings given above are reacted with sulphonamide derivatives of the general formula (VI)

$$R^3\text{—}SO_2\text{—}NH\text{—}CQ^2\text{—}Z \qquad (VI)$$

in which
- $Q^2$ and $R^3$ have the meanings given above and
- Z represents halogen, alkoxy, aralkoxy or aryloxy, optionally in the presence of an acid acceptor and optionally in the presence of a diluent, or if (d) triazolin(thi)ones of the general formula (II)

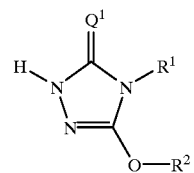

(II)

in which
$Q^1$, $R^1$ and $R^2$ have the meanings given above are reacted with sulphonyl halides of the general formula (VII)

$$R^3\text{—}SO_2\text{—}X \qquad (VII)$$

in which

R³ has the meaning given above and

X represents halogen and with metal (thio)cyanates of the general formula (VIII)

$$MQ^2CN \quad (VIII)$$

in which

Q² has the meaning given above and

M represents an alkali metal or alkaline earth metal equivalent, optionally in the presence of a reaction auxiliary and optionally in the presence of a diluent, and if desired the compounds of the formula (I) obtained by process (a), (b), (c) or (d) are converted into salts by customary methods.

The novel sulphonylamino(thio)carbonyltriazolin(thi)ones having heterocyclyl(alk)oxy substituents, of the general formula (I), are distinguished by a strong herbicidal activity.

The invention relates preferably to compounds of the formula (I) in which $Q^1$ represents oxygen or sulphur, $Q^2$ represents oxygen or sulphur, $R^1$ represents hydrogen, hydroxyl, amino or $C_1$–$C_6$-alkylideneamino, or represents optionally fluoro-, chloro-, bromo-, cyano-, $C_1$–$C_4$-alkoxy-, $C_1$–$C_4$-alkylcarbonyl- or $C_1$–$C_4$-alkoxy-carbonyl-substituted $C_1$–$C_6$-alkyl, or represents in each case optionally fluoro-, chloro- and/or bromo-substituted $C_2$–$C_6$-alkenyl or $C_2$–$C_6$-alkinyl, or represents $C_1$–$C_6$-alkyloxy or $C_3$–$C_6$-alkenyloxy, or represents in each case optionally fluoro- and/or chloro-substituted $C_1$–$C_6$-alkylamino, di-($C_1$–$C_4$-alkyl)-amino or $C_1$–$C_4$-alkanoylamino, or represents in each case optionally fluoro-, chloro-, bromo- and/or $C_1$–$C_4$-alkyl-substituted $C_3$–$C_6$-cycloalkyl or $C_3$–$C_6$-cycloalkyl-$C_1$–$C_4$-alkyl, or represents in each case optionally fluoro-, chloro-, bromo-, cyano-, nitro-, $C_1$–$C_4$-alkyl-, trifluoromethyl-, $C_1$–$C_4$-alkoxy- and/or $C_1$–$C_4$-alkoxy-carbonyl-substituted phenyl or phenyl-$C_1$–$C_4$-alkyl, $R^2$ represents in each case optionally halogeno- and/or $C_1$–$C_4$-alkyl-substituted oxetanyl, thietanyl, furyl, tetrahydrofuryl, thienyl, tetrahydrothienyl, pyridyl, pyrimidyl, oxetanyl-$C_1$–$C_4$-alkyl, thietanyl-$C_1$–$C_4$-alkyl, furyl-$C_1$–$C_4$-alkyl, tetrahydrofuryl-$C_1$–$C_4$-alkyl, thienyl-$C_1$–$C_4$-alkyl, tetrahydrothienyl-$C_1$–$C_4$-alkyl, pyridyl-$C_1$–$C_4$-alkyl or pyrimidyl-$C_1$–$C_4$-alkyl, and $R^3$ represents the group

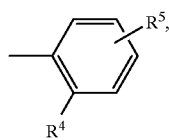

in which $R^4$ and $R^5$ are identical or different and represent hydrogen, fluoro, chloro, bromo, iodo, nitro or $C_1$–$C_6$-alkyl (which is optionally substituted by fluoro, chloro, bromo, cyano, carboxyl, $C_1$–$C_4$-alkoxycarbonyl, $C_1$–$C_4$-alkylamino-carbonyl, di-($C_1$–$C_4$-alkyl)-amino-carbonyl, hydroxyl, $C_1$–$C_4$-alkoxy, formyloxy, $C_1$–$C_4$-alkyl-carbonyloxy, $C_1$–$C_4$-alkoxy-carbonyloxy, $C_1$–$C_4$-alkylamino-carbonyloxy, $C_1$–$C_4$-alkylthio, $C_1$–$C_4$-alkylsulphinyl, $C_1$–$C_4$-alkylsulphonyl, di-($C_1$–$C_4$-alkyl)-amino-sulphonyl, $C_3$–$C_6$-cycloalkyl or phenyl), or represent $C_2$–$C_6$-alkenyl (which is optionally substituted by fluoro, chloro, bromo, cyano, $C_1$–$C_4$-alkoxy-carbonyl, carboxyl or phenyl), or represent $C_2$–$C_6$-alkinyl (which is optionally substituted by fluoro, chloro, bromo, cyano, $C_1$–$C_4$-alkoxy-carbonyl, carboxyl or phenyl), or represent $C_1$–$C_4$-alkoxy (which is optionally substituted by fluoro, chloro, bromo, cyano, carboxyl, $C_1$–$C_4$-alkoxy-carbonyl, $C_1$–$C_4$-alkoxy, $C_1$–$C_4$-alkylthio, $C_1$–$C_4$-alkylsulphinyl or $C_1$–$C_4$-alkylsulphonyl), or represent $C_1$–$C_4$-alkylthio (which is optionally substituted by fluoro, chloro, bromo, cyano, carboxyl, $C_1$–$C_4$-alkoxy-carbonyl, $C_1$–$C_4$-alkylthio, $C_1$–$C_4$-alkylsulphinyl or $C_1$–$C_4$-alkylsulphonyl), or represent $C_2$–$C_6$-alkenyloxy (which is optionally substituted by fluoro, chloro, bromo, cyano or $C_1$–$C_4$-alkoxy-carbonyl), or represent $C_2$–$C_6$-alkenylthio (which is optionally substituted by fluoro, chloro, bromo, cyano, nitro, $C_1$–$C_3$-alkylthio or $C_1$–$C_4$-alkoxy-carbonyl), $C_3$–$C_6$-alkinyloxy or $C_3$–$C_6$-alkinylthio, or represent the radical —S(O)$_p$—R⁶, where p represents the numbers 1 or 2 and $R^6$ represents $C_1$–$C_4$-alkyl (which is optionally substituted by fluoro, chloro, bromo, cyano or $C_1$–$C_4$-alkoxy-carbonyl), $C_3$–$C_6$-alkenyl, C3–$C_6$-alkinyl, $C_1$–$C_4$-alkoxy, $C_1$–$C_4$-alkoxy-$C_1$–$C_4$-alkylamino, $C_1$–$C_4$-alkylamino, di-($C_1$–$C_4$-alkyl)-amino or phenyl or represents the radical —NHOR⁷, where $R^7$ represents $C_1$–$C_{12}$-alkyl (which is optionally substituted by fluoro, chloro, cyano, $C_1$–$C_4$-alkoxy, $C_1$–$C_4$-alkylthio, $C_1$–$C_4$-alkylsulphinyl, $C_1$–$C_4$-alkylsulphonyl, $C_1$–$C_4$-alkyl-carbonyl, $C_1$–$C_4$-alkoxycarbonyl, $C_1$–$C_4$-alkylamino-carbonyl or Di-($C_1$–$C_4$-alkyl)-amino-carbonyl), or represents $C_3$–$C_6$-alkenyl (which is optionally substituted by fluoro, chloro or bromo), $C_3$–$C_6$-alkinyl, $C_3$–$C_6$-cycloalkyl, $C_3$–$C_6$-cycloalkyl-$C_1$–$C_2$-alkyl or phenyl-$C_1$–$C_2$-alkyl (which is optionally substituted by fluoro, chloro, nitro, cyano, $C_1$–$C_4$-alkyl, $C_1$–$C_4$-alkoxy or $C_1$–$C_4$-alkoxycarbonyl), or represents benzhydryl or represents phenyl (which is optionally substituted by fluoro, chloro, nitro, cyano, $C_1$–$C_4$-alkyl, trifluoromethyl, $C_1$–$C_4$-alkoxy, $C_1$–$C_2$-fluoroalkoxy, $C_1$–$C_4$-alkylthio, trifluoromethylthio or $C_1$–$C_4$-alkoxy-carbonyl), $R^4$ and/or $R^5$ additionally represent phenyl or phenoxy, or represent $C_1$–$C_4$-alkylcarbonylamino, $C_1$–$C_4$-alkoxy-carbonylamino, $C_1$–$C_4$-alkylamino-carbonylamino or di-($C_1$–$C_4$-alkyl)-aminocarbonylamino, or represent the radical —CO—R⁸, where $R^8$ represents hydrogen, $C_1$–$C_6$-alkyl, $C_3$–$C_6$-cycloalkyl, $C_1$–$C_6$-alkoxy, $C_3$–$C_6$-cycloalkoxy, $C_3$–$C_6$-alkenyloxy, $C_1$–$C_4$-alkylthio, $C_1$–$C_4$-alkylamino, $C_1$–$C_4$-alkoxyamino, $C_1$–$C_4$-alkoxy-$C_1$–$C_4$-alkylamino or di-($C_1$–$C_4$-alkyl)-amino (which are optionally substituted by fluoro and/or chloro), $R^4$ and/or $R^5$ additionally represent trimethylsilyl, thiazolinyl, $C_1$–$C_4$-alkylsulphonyloxy or di-($C_1$–$C_4$-alkyl)-aminosulphonylamino or represent the radical

—CH=N—R⁹, where
R⁹ represents optionally fluoro-, chloro-, cyano-, carboxyl-, $C_1$–$C_4$-alkoxy-, $C_1$–$C_4$-alkylthio-, $C_1$–$C_4$-alkylsulphinyl- or $C_1$–$C_4$-alkylsulphonyl-substituted $C_1$–$C_6$-alkyl, or represents optionally fluoro- or chloro-substituted benzyl, or represents optionally fluoro- or chloro-substituted $C_3$–$C_6$-alkenyl or $C_3$–$C_6$-alkinyl, or represents optionally fluoro-, chloro-, bromo-, $C_1$–$C_4$-alkyl-, $C_1$–$C_4$-alkoxy-, trifluoromethyl-, trifluoromethoxy- or trifluoromethylthio-substituted phenyl, or represents optionally fluoro- and/or chloro-substituted $C_1$–$C_6$-alkoxy, $C_3$–$C_6$-alkenyloxy, $C_3$–$C_6$-alkinyloxy or benzyloxy, or represents amino, $C_1$–$C_4$-alkylamino, di-($C_1$–$C_4$-alkyl)-amino, phenylamino, $C_1$–$C_4$-alkylcarbonylamino, $C_1$–$C_4$-alkoxycarbonylamino or $C_1$–$C_4$-alkyl-sulphonylamino or represents optionally fluoro-, chloro-, bromo- or methyl-substituted phenylsulphonylamino, and also $R^3$ represents the radical

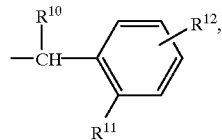

in which
$R^{10}$ represents hydrogen or $C_1$–$C_4$-alkyl,
$R^{11}$ and $R^{12}$ are identical or different and represent hydrogen, fluoro, chloro, bromo, nitro, cyano, $C_1$–$C_4$-alkyl (which is optionally substituted by fluoro and/or chloro), $C_1$–$C_4$-alkoxy (which is optionally substituted by fluoro and/or chloro), carboxyl, $C_1$–$C_4$-alkoxy-carbonyl, dimethylaminocarbonyl, $C_1$–$C_4$-alkylsulphonyl or di-($C_1$–$C_4$-alkyl)-aminosulphonyl;

and also $R^3$ represents the radical

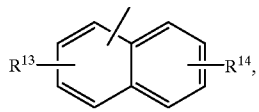

in which
$R^{13}$ and $R^{14}$ are identical or different and represent hydrogen, fluoro, chloro, bromo, nitro, cyano, $C_1$–$C_4$-alkyl (which is optionally substituted by fluoro and/or chloro) or $C_1$–$C_4$-alkoxy (which is optionally substituted by fluoro and/or chloro);

and also $R^3$ represents the radical

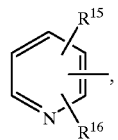

in which
$R^{15}$ and $R^{16}$ are identical or different and represent hydrogen, fluoro, chloro, bromo, nitro, cyano, $C_1$–$C_4$-alkyl (which is optionally substituted by fluoro and/or chloro), $C_1$–$C_4$-alkoxy (which is optionally substituted by fluoro and/or chloro), or represent $C_1$–$C_4$-alkylthio, $C_1$–$C_4$-alkylsulphinyl or $C_1$–$C_4$-alkylsulphonyl (which are optionally substituted by fluoro and/or chloro) or represent aminosulphonyl or mono-($C_1$–$C_4$-alkyl)-aminosulphonyl, or represent di-($C_1$–$C_4$-alkyl)-aminosulphonyl or $C_1$–$C_4$-alkoxy-carbonyl or dimethylaminocarbonyl;

and also $R^3$ represents the radical

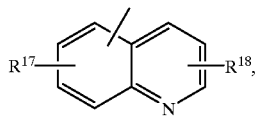

in which
$R^{17}$ and $R^{18}$ are identical or different and represent hydrogen, fluoro, chloro, bromo, $C_1$–$C_4$-alkyl (which is optionally substituted by fluoro and/or bromo) or $C_1$–$C_4$-alkoxy (which is optionally substituted by fluoro and/or chloro), or represent $C_1$–$C_4$-alkylthio, $C_1$–$C_4$-alkylsulphinyl or $C_1$–$C_4$-alkylsulphonyl (which are optionally substituted by fluoro and/or chloro), or represent di-($C_1$–$C_4$-alkyl)-aminosulphonyl;

and also $R^3$ represents the radical

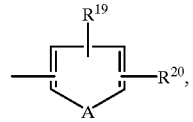

in which
$R^{19}$ and $R^{20}$ are identical or different and represent hydrogen, fluoro, chloro, bromo, cyano, nitro, $C_1$–$C_4$-alkyl (which is optionally substituted by fluoro and/or chloro), $C_1$–$C_4$-alkoxy (which is optionally substituted by fluoro and/or chloro), $C_1$–$C_4$-alkylthio, $C_1$–$C_4$-alkylsulphinyl or $C_1$–$C_4$-alkylsulphonyl (which are optionally substituted by fluoro and/or chloro), di-($C_1$–$C_4$-alkyl)-aminosulphonyl, $C_1$–$C_4$-alkoxy-carbonyl or dimethylaminocarbonyl, and
A represents oxygen, sulphur or the group N-$Z^1$, where $Z^1$ represents hydrogen, $C_1$–$C_4$-alkyl (which is optionally substituted by fluoro, chloro, bromo or cyano), $C_3$–$C_6$-cycloalkyl, benzyl, phenyl (which is optionally substituted by fluoro, chloro, bromo or nitro), $C_1$–$C_4$-alkylcarbonyl, $C_1$–$C_4$- alkoxycarbonyl or di-($C_1$-$C_4$-alkyl)-aminocarbonyl;

and also $R^3$ represents the radical

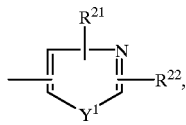

in which $R^{21}$ and $R^{22}$ are identical or different and represent hydrogen, $C_1$-$C_4$-alkyl, halogen, $C_1$-$C_4$-alkoxycarbonyl, $C_1$-$C_4$-alkoxy or $C_1$-$C_4$-halogenoalkoxy, $Y^1$ represents sulphur or the group N-$R^{23}$, where $R^{23}$ represents hydrogen or $C_1$-$C_4$-alkyl;

and also $R^3$ represents the radical

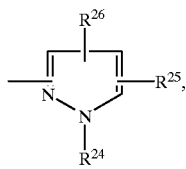

in which $R^{24}$ represents hydrogen, $C_1$-$C_4$-alkyl, benzyl, pyridyl, quinolyl or phenyl, $R^{25}$ represents hydrogen, halogen, cyano, nitro, $C_1$-$C_4$-alkyl (which is optionally substituted by fluoro and/or chloro), $C_1$-$C_4$-alkoxy (which is optionally substituted by fluoro and/or chloro), dioxolanyl or $C_1$-$C_4$-alkoxy-carbonyl, and $R^{26}$ represents hydrogen, halogen or $C_1$-$C_4$-alkyl.

The invention additionally relates preferably to sodium salts and to potassium, magnesium, calcium, ammonium, $C_1$-$C_4$-alkyl-ammonium, di-($C_1$-$C_4$-alkyl)-ammonium, tri-($C_1$-$C_4$-alkyl)-ammonium, tetra-($C_1$-$C_4$-alkyl)-ammonium, tri-($C_1$-$C_4$-alkyl)-sulphonium, $C_5$- or $C_6$-cycloalkyl-ammonium and di-($C_1$-$C_2$-alkyl)-benzyl-ammonium salts of compounds of the formula (I) in which $Q^1$, $Q^2$, $R^1$, $R^2$ and $R^3$ have the meanings given above as preferred.

The invention relates in particular to compounds of the formula (I) in which $Q^1$ represents oxygen or sulphur, $Q^2$ represents oxygen or sulphur, $R^1$ represents in each case optionally fluoro-, chloro-, cyano-, methoxy- or ethoxy-substituted methyl, ethyl, n- or i-propyl, n-, i-, s- or t-butyl, or represents in each case optionally fluoro-, chloro- or bromo-substituted propenyl, butenyl, propinyl or butinyl, or represents methoxy, ethoxy, n- or i-propoxy or represents allyloxy, or represents methylamino, ethylamino, n- or i-propylamino, n-, i-, s- or t-butylamino, dimethylamino or diethylamino, or represents in each case optionally fluoro-, chloro-, bromo-, methyl- or ethyl-substituted cyclopropyl, cyclobutyl, cyclopentyl, cyclohexyl, cyclopropylmethyl, cyclobutylmethyl, cyclopentylmethyl or cyclohexylmethyl, or represents in each case optionally fluoro-, chloro-, bromo-, cyano-, methyl-, trifluoromethyl- or methoxy-substituted benzyl or phenyl, $R^2$ represents in each case optionally fluoro- and/or chloro-, methyl- and/or ethyl-substituted oxetanyl, thietanyl, furyl, tetrahydrofuryl, thienyl, tetrahydrothienyl, oxetanylmethyl, thietanylmethyl, furylmethyl, tetrahydrofurylmethyl, thienylmethyl or tetrahydrothienylmethyl, and $R^3$ represents the radical

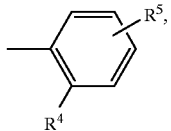

in which $R^4$ represents fluoro, chloro, bromo, methyl, ethyl, n- or i-propyl, trifluoromethyl, methoxy, ethoxy, n- or i-propoxy, n- or i-butoxy, difluoromethoxy, trifluoromethoxy, 2-chloro-ethoxy, 2,2,2-trifluoro-ethoxy, 1,1,2,2-tetrafluoro-ethoxy, 1,1,2,2,2-pentafluoro-ethoxy, 2-methoxy-ethoxy, methylthio, ethylthio, n- or i-propylthio, n- or i-butylthio, 2-fluoro-ethylthio, allyloxy, propargyloxy, methylsulphinyl, ethylsulphinyl, methylsulphonyl, ethylsulphonyl, dimethylaminosuiphonyl, diethylaminosulphonyl, N-methoxy-N-methylaminosulphonyl, phenyl, phenoxy, methoxycarbonyl, ethoxycarbonyl, n- or i-propoxycarbonyl, and $R^5$ represents hydrogen, fluoro, chloro, bromo, methyl, ethyl, n- or i-propyl, trifluoromethyl, methoxy, ethoxy, n- or i-propoxy, difluoromethoxy, trifluoromethoxy, methylthio or ethylthio;

and also $R^3$ represents the radical

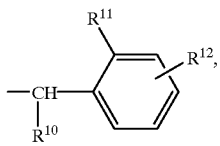

in which $R^{10}$ represents hydrogen, $R^{11}$ represents fluoro, chloro, bromo, methyl, methoxy, difluoromethoxy, trifluoromethoxy, ethoxy, methoxycarbonyl, ethoxycarbonyl, methylsulphonyl or dimethylaminosulphonyl, and $R^{12}$ represents hydrogen;

and also $R^3$ represents the radical

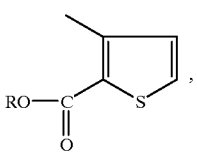

in which

R represents methyl, ethyl, n- or i-propyl, or $R^3$ represents the radical

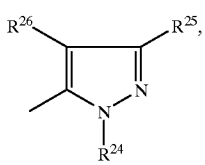

in which
$R^{24}$ represents methyl, ethyl, n- or i-propyl, phenyl or pyridyl,
$R^{25}$ represents hydrogen, fluoro, chloro or bromo,
$R^{26}$ represents fluoro, chloro, bromo, methoxycarbonyl or ethoxycarbonyl.

The radical definitions listed above, given generally or in ranges of preference, apply not only to the end products of the formula (I) but also, correspondingly, to the starting materials and/or intermediates required in each case for preparation. These radical definitions can be combined as desired with one another, thus including combinations between the stated ranges of preferred compounds.

The hydrocarbon radicals mentioned in the radical definitions, such as alkyl, alkenyl or alkinyl, alone or in combination with heteroatoms such as in alkoxy, alkylthio or alkylamino, are straight-chain or branched even if this is not expressly indicated.

Halogen represents generally fluoro, chloro, bromo or iodo, preferably fluoro, chloro, or bromo, and especially fluoro or chloro.

Using, for example, 2-trifluoromethoxy-phenylsulphonyl isocyanate and 4-phenyl-5-(oxetan-3-yl-oxy)-2,4-dihydro-3H-1,2,4-triazol-3-one as starting materials, the course of reaction in the process (a) according to the invention can be illustrated by the following equation:

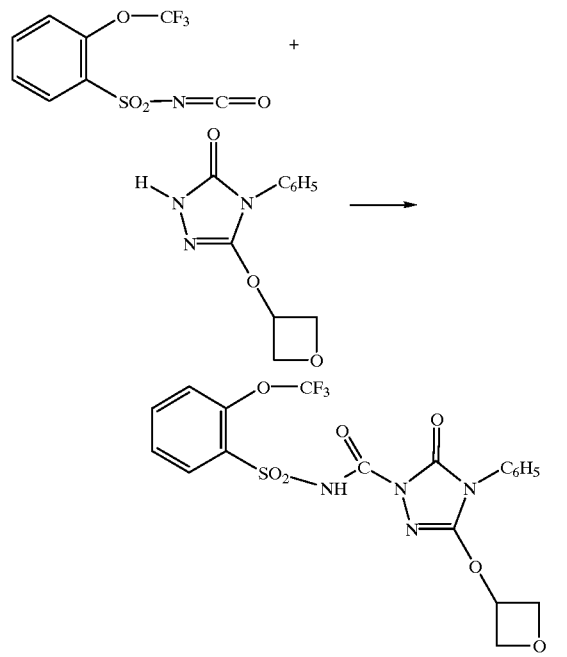

Using, for example, 2-ethylthio-benzenesulphonamide and 2-chlorocarbonyl-4-cyclohexyl-5-(thietan-3-yl-oxy)-2,4-dihydro-3H-1,2,4-triazol-3-one as starting materials, the course of reaction in the process (b) according to the invention can be illustrated by the following equation:

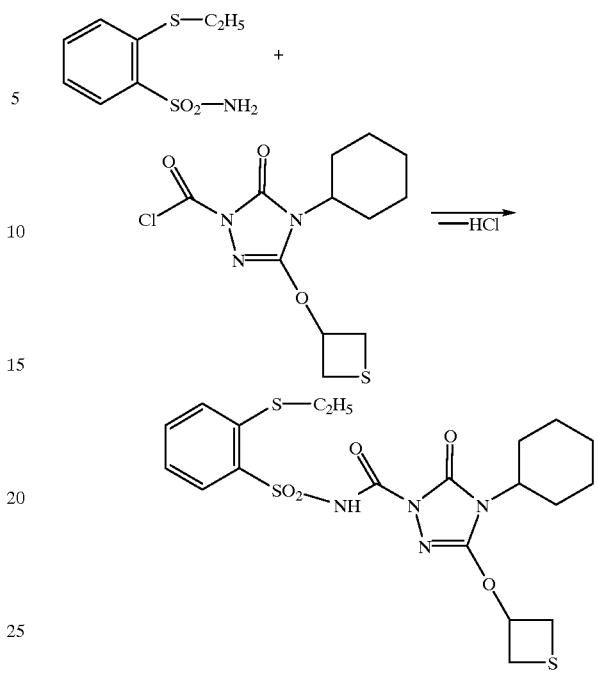

Using, for example N-methoxycarbonyl-2-methoxy-benzenesulphonamide and 5-(tetrahydro-2-furyl-methoxy)-4-methyl-2,4-dihydro-3H-1,2,4-triazol-3-one as starting materials, the course of reaction in the process (c) according to the invention can be illustrated by the following equation:

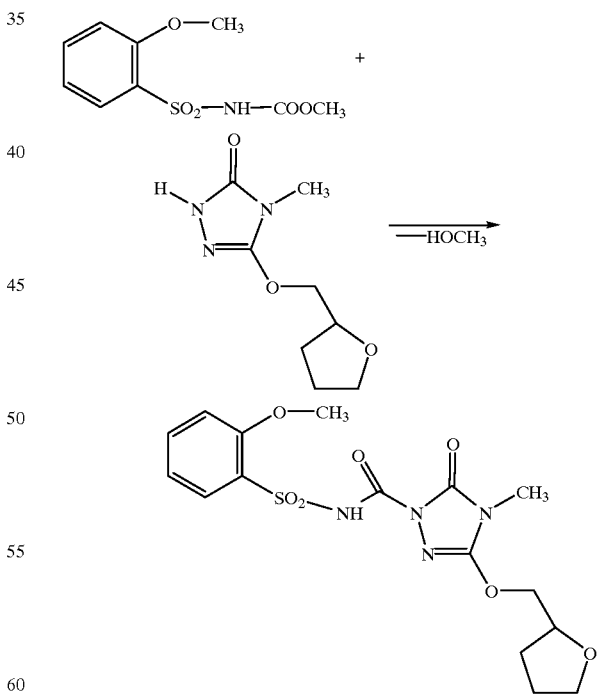

Using, for example, 2-chloro-6-methyl-benzenesulphonyl chloride, 4-allyl-5-(tetrahydrothienyl-3-oxy)-2,4-dihydro-3H-1,2,4-triazol-3-one and sodium cyanate as starting materials, the course of reaction in the process (d) according to the invention can be illustrated by the following equation:

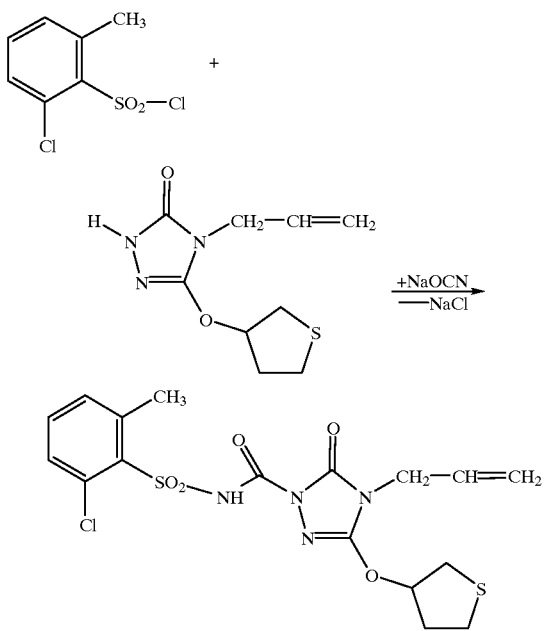

A general definition of the triazolin(thi)ones to be used as starting materials in the processes (a), (c) and (d) according to the invention for the preparation of compounds of the formula (I) is given by the formula (II).

In the formula (II), $Q^1$, $R^1$ and $R^2$ preferably or in particular have those meanings which have already been indicated above, in connection with the description of the compounds of the formula (I) according to the invention, as being preferable or particularly preferable for $Q^1$, $R^1$ and $R^2$.

The triazolin(thi)ones of the general formula (II) have not yet been disclosed in the literature; as novel substances, they are also part of the present application.

The novel triazolin(thi)ones of the formula (II) are obtained if (thio)carbazinic esters of the general formula (IX)

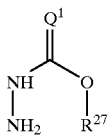

(IX)

in which
$Q^1$ has the meaning given above and
$R^{27}$ represents optionally substituted alkyl (preferably methyl, ethyl, methoxyethyl or ethoxyethyl) or represents phenyl are reacted with alkyliminocarbonic acid diesters of the general formula (X)

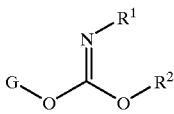

(X)

in which
$R^1$ and $R^2$ have the meanings given above and

G represents alkyl (preferably methyl or ethyl) or has the same meaning as $R^2$, optionally in the presence of a diluent, for example methanol, and optionally in the presence of a reaction auxiliary, for example pivalic acid, at temperatures between 0° C. and 100° C., and the compounds formed in this reaction, of the general formula (XI)

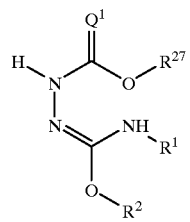

(XI)

in which
$Q^1$, $R^1$, $R^2$ and $R^{27}$ have the meanings given above
are subjected—optionally after intermediate isolation—to cyclizing condensation, optionally in the presence of a diluent, for example methanol, and optionally in the presence of a reaction auxiliary, for example sodium methylate, at temperatures between 20° C. and 150° C. (cf. the preparation examples).

A general definition of the sulphonyl iso(thio)cyanates also to be used as starting materials in the process (a) according to the invention for the preparation of compounds of the formula (I) is given by the formula (III).

In the formula (III), $Q^2$ and $R^3$ preferably or in particular have those meanings which have already been indicated above, in connection with the description of the compounds of the formula (I) according to the invention, as being preferable or particularly preferable for $Q^2$ and $R^3$.

The starting materials of the formula (III) are known and/or can be prepared by methods known per se (cf. U.S. Pat. Nos. 4,127,405, 4,169,719, 4,371,391, EP A 7 687, EP-A 13 480, EP-A 21 641, EP-A 23 141, EP-A 23 422, EP-A 30 139, EP-A 35 893, EP-A 44 808, EP-A 44 809, EP-A 48 143, EP-A 51 466, EP-A 64 322, EP-A 70 041, EP-A 173 312).

A general definition of the triazolin(thi)one derivatives to be used as starting materials in the process (b) according to the invention for the preparation of the compounds of the general formula (I) is given by the formula (IV). In the formula (IV), $Q^1$, $Q^2$, $R^1$ and $R^2$ preferably or in particular have those meanings which have already been indicated above, in connection with the description of the compounds of the formula (I), as being preferable or particularly preferable for $Q^1$, $Q^2$, $R^1$ and $R^2$; Z preferably represents fluoro, chloro, bromo, methoxy, ethoxy, benzyloxy, phenoxy, halogeno- or nitro-phenoxy, in particular methoxy, phenoxy or 4-nitro-phenoxy.

The starting materials of the formula (IV) have not yet been disclosed in the literature; as novel substances, they are likewise part of the present application.

The novel compounds of the formula (IV) are obtained if triazolin(thi)ones of the general formula (II)

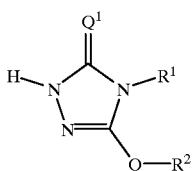

(II)

in which
Q¹, R¹ and R² have the meanings given above
are reacted with carbonic acid derivatives of the general formula (XII)

$$Z-CQ^2-Z^1 \quad (XII)$$

in which
Q² and Z have the meanings given above and
Z¹ represents halogen (especially chloro), alkoxy (especially methoxy), aralkoxy (especially benzyloxy) or aryloxy (especially phenoxy),
optionally in the presence of an acid acceptor, for example sodium hydride or potassium hydride, sodium hydroxide or potassium hydroxide, sodium t-butylate or potasssium t-butylate, and optionally in the presence of a diluent, for example tetrahydrofuran or dimethoxyethane, or in a two-phase system comprising water and an organic solvent, for example methylene chloride or chloroform, at temperatures between 0° C. and 100° C.

A general definition of the sulphonamides also to be used as starting materials in the process (b) according to the invention for the preparation of the compounds of the general formula (I) is given by the formula (V). In the formula (V), R³ preferably or in particular has that meaning which has already been indicated above, in connection with the description of the compounds of the formula (I), as being preferable or particularly preferable for R³.

The starting materials of the formula (V) are known and/or can be prepared by methods known per se (cf. U.S. Pat. Nos. 4,127,405, 4,169,719, 4,371,391, EP-A 7 687, EP-A 13 480, EP-A 21 641, EP-A 23 141, EP-A 23 422, EP-A 30 139, EP-A 35 893, EP-A 44 808, EP-A 44 809, EP-A 48 143, EP-A 51 466, EP-A 64 322, EP-A 70 041, EP-A 173 312).

A general definition of the sulphonamide derivatives to be used as starting materials in the process (c) according to the invention for the preparation of the compounds of the formula (I) is given by the formula (VI). In the formula (VI), Q² and R³ preferably or in particular have those meanings which have already been indicated above, in connection with the description of the compounds of the formula (I), as being preferable or particularly preferable for Q² and R³; Z preferably represents fluoro, chloro, bromo, methoxy, ethoxy, benzyloxy, or phenoxy, especially methoxy or phenoxy.

The starting materials of the formula (VI) are known and/or can be prepared by methods known per se.

A general definition of the sulphonyl halides to be used as starting materials in the process (d) according to the invention for the preparation of the compounds of the formula (I) is given by the formula (VII). In the formula (VII), R³ preferably or in particular has that meaning which has already been indicated above, in connection with the description of the compounds of the formula (I), as being preferable or particularly preferable for R³; X preferably represents fluoro, chloro or bromo, especially chloro.

The starting materials of the formula (VII) are known and/or can be prepared by methods known per se.

The processes (a), (b), (c) and (d) according to the invention for the preparation of the novel compounds of the formula (I) are preferably carried out using diluents. Suitable diluents in this context are virtually all inert organic solvents. These include, preferably, aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, tetrachloromethane, chlorobenzene and o-dichlorobenzene; ethers such as diethyl ether and dibutyl ether, glycol dimethyl ether and diglycol dimethyl ether, tetrahydrofuran and dioxane; ketones such as acetone, methyl ethyl ketone, methyl isopropyl ketone and methyl isobutyl ketone; esters such as methyl acetate and ethyl acetate; nitriles, for example acetonitrile and propionitrile; amides, for example dimethylformamide, dimethylacetamide and N-methyl-pyrrolidone, and also dimethyl sulphoxide, tetramethylene sulphone and hexamethylphosphoric triamide.

As reaction auxiliaries and/or as acid acceptors, it is possible in the processes (a), (b), (c) and (d) according to the invention to employ all acid-binding agents which can customarily be used for such reactions. Suitable examples are preferably alkali metal hydroxides such as sodium hydroxide and potassium hydroxide, alkaline earth metal hydroxides, for example calcium hydroxide, alkali metal carbonates and alkali metal alcoholates, such as sodium carbonate and potassium carbonate, sodium tert-butylate and potassium tert-butylate, and also basic nitrogen compounds, such as trimethylamine, triethylamine, tripropylamine, tributylamine, diisobutylamine, dicyclohexylamine, ethyldiisopropylamine, ethyldicyclohexylamine, N,N-dimethylbenzylamine, N,N-dimethyl-aniline, pyridine, 2-methyl-, 3-methyl-, 4-methyl-, 2,4-dimethyl-, 2,6-dimethyl-, 2-ethyl-, 4-ethyl- and 5-ethyl-2-methyl-pyridine, 1,5-diazabicyclo[4.3.0]-non-5-ene (DBN), 1,8-diazabicyclo [5.4.0]-undec-7-ene (DBU) and 1,4-diazabicyclo-[2.2.2]-octane (DABCO).

The reaction temperatures in the processes (a), (b), (c) and (d) according to the invention can be varied within a relatively large range. The processes are in general carried out at temperatures between –20° C. and +100° C., preferably at temperatures between 0° C. and +80° C.

The processes (a), (b), (c) and (d) according to the invention are in general carried out under atmospheric pressure. However, it is also possible to operate under increased or reduced pressure.

For carrying out the processes (a), (b), (c) and (d) according to the invention, the starting materials required in each case are in general employed in approximately equimolar quantities. However, it is also possible to use one of the components employed in each case in a relatively large excess. The reactions are in general carried out in a suitable diluent in the presence of an acid acceptor, and the reaction mixture is stirred for a number of hours at the particular temperature required. Working up in the case of the processes (a), (b), (c) and (d) according to the invention takes place in each case by customary methods (cf. the preparation examples).

From the compounds of the general formula (I) according to the invention it is possible, if desired, to prepare salts. Such salts are obtained in a simple manner by customary methods of salt formation, for example by dissolving or dispersing a compound of the formula (I) in an appropriate solvent, for example methylene chloride, acetone, tert-butyl methyl ether or toluene, and adding an appropriate base. The salts can then—optionally after prolonged stirring—be isolated by concentration or filtration with suction.

The active compounds according to the invention can be used as defoliants, desiccants, agents for destroying broad-leaved plants and, especially, as weed-killers. By weeds, in the broadest sense, there are to be understood all plants which grow in locations where they are not wanted. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium. However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture-land, and for the selective combating of weeds in annual cultures.

The compounds of the formula (I) according to the invention are particularly suitable for the selective combating of monocotyledon and dicotyledon weeds in monocotyledon and dicotyledon crops, both pre-emergence and post-emergence.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural minerals such as calcite, marble, pumice, sepiolite and dolomite, as well as synthetic granules of inorganic and organic meals, and granules of organic material such as sawdust, coconut shells, maize cobs and tobacco stalks; as emulsifying and/or foamforming agents there are suitable: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example ligninsulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colourants such as inorganic pigments, for example iron oxide, titanium oxide and Prussian Blue, and organic dyes, such as alizarin dyes, azo dyes and metal phthalocyanine dyes, and trace nutrients such as salts of iron, manganese, boron, copper, cobalt, molybdenum and zinc.

The formulations in general contain between 0.1 and 95 per cent by weight of active compound, preferably between 0.5 and 90%.

For combating weeds, the active compounds according to the invention, as such or in the form of their formulations, can also be used as mixtures with known herbicides, finished formulations or tank mixes being possible.

Suitable co-components for the mixtures are known herbicides, for example anilides, for example diflufenican and propanil; arylcarboxylic acids, for example dichloropicolinic acid, dicamba and picloram; aryloxyalkanoic acids, for example 2,4-D, 2,4-DB, 2,4-DP, fluroxypyr, MCPA, MCPP and triclopyr; aryloxy-phenoxy alkanoic esters for example diclofop-methyl, fenoxaprop-ethyl, fluazifop-butyl, haloxyfop-methyl and quizalofop-ethyl; azinones, for example chloridazone and norflurazone; carbamates, for example chlorpropham, desmedipham, phenmedipham and propham; chloroacetanilides, for example alachlor, acetochlor, butachlor, metazachlor, metolachlor, pretilachlor and propachlor; dinitroanilines, for example oryzalin, pendimethalin and trifluralin; diphenyl ethers, for example acifluorfen, bifenox, fluoroglycofen, fomesafen, halosafen, lactofen and oxyfluorfen; ureas, for example chlorotoluron, diuron, fluometuron, isoproturon, linuron and methabenzthiazuron; hydroxylamines, for example alloxydim, clethodim, cycloxydim, sethoxydim and tralkoxydim;

imidazolinones, for example imazethapyr, imazamethabenz, imazapyr and imazaquin; nitriles, for example bromoxynil, dichlobenil and ioxynil; oxyacetamides, for example mefenacet; sulphonyl ureas, for example amidosulfuron, bensulfuron-methyl, chlorimuronethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl; thiolcarbamates, for example butylate, cycloate, diallate, EPTC, esprocarb, molinate, prosulfocarb, thiobencarb and triallate; triazines, for example atrazine, cyanazine, simazine, simetryne, terbutryne and terbutylazine; triazinones, for example hexazinone, metamitron and metribuzin; others, for example aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 1 g and 10 kg of active compound per hectare of soil surface, preferably between 5 g and 2 kg per ha.

The preparation and use of the active compounds according to the invention can be seen from the following examples.

PREPARATION EXAMPLES

Example 1

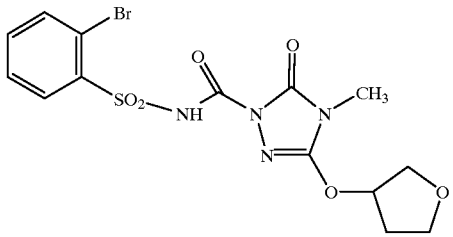

(Process (a))

A mixture of 1.3 g (7 mmol) of 4-methyl-5-(3-tetrahydrofuryi-oxy)-2,4-dihydro-3H-1,2,4-triazol-3-one, 2.24 g (8.4 mmol) of 2-trifluoromethoxy-phenylsulphonyl isocyanate and 60 ml of acetonitrile is stirred at about 20° C. for 16 hours. It is then concentrated under a water pump vacuum, the residue is stirred with isopropanol/petroleum ether (volume about 3/7) and the crystalline product obtained in this procedure is isolated by filtration with suction.

3.0 g (94% of theory) of 4-methyl-5-(3-tetrahydrofuryl-oxy)-2-(2-trifluoromethoxy-phenylsulphonylaminocarbonyl)-2,4-dihydro-3H-1,2,4-triazol-3-one are obtained of melting point 184° C.

Example 2

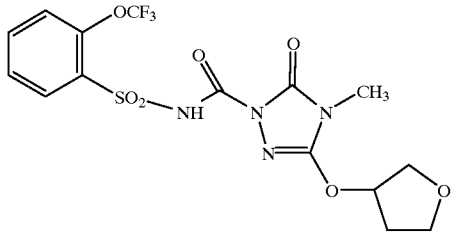

(Process (b))

2.5 g (10 mmol) of 2-bromo-benzolsulphonamide are dissolved in 40 ml acetonitrile, and 3.2 g (10 mmol) of 4-methyl-2-phenoxycarbonyl-5-(3-tetrahydrofuryl-oxy)-2,4-dihydro-3H-1,2,4-triazol-3-one and 1.6 g (10 mmol) of diazabicycloundecene (DBU) are added with strirring. The mixture is stirred at 20° C. for 12 hours and then concentrated under a water pump vacuum. The residue is taken up in methylene chloride and the mixture is washed with 10% strength hydrochloric acid, dried over sodium sulphate and filtered. The filtrate is concentrated under a water pump vacuum, the residue is digested with isopropanol/petroleum ether (1/5) and the crystalline product obtained is isolated by filtration with suction.

3.5 g (78% of theory) of 2-(2-bromo-phenylsulphonyl-aminocarbonyl)-4-methyl-5-(3-tetrahydrofuryl-oxy)-2,4-dihydro-3H-1,2,4-triazol-3-one are obtained of melting point 191° C.

In analogy to Example 1 or 2 and in accordance with the general description of the preparation processes according to the invention it is also possible, for example, to prepare the compounds of the formula (I) which are listed in Table I below.

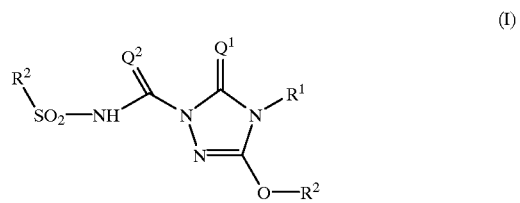

(I)

TABLE 1

Examples of the compounds of the formula (I)

| Ex. No. | $Q^1$ | $Q^2$ | $R^1$ | $R^2$ | $R^3$ | Melting point (° C.) |
|---|---|---|---|---|---|---|
| 3 | O | O | $CH_3$ | 5-methyl-2-tert-butyl-pyrimidin-yl | 2-(OCHF$_2$)phenyl | 185 |
| 4 | O | O | $CH_3$ | tetrahydrofuran-3-yl | 2-(OCH$_3$)phenyl | 178 |
| 5 | O | O | $CH_3$ | tetrahydrofuran-3-yl | 2-(CH$_3$)phenyl | 187 |
| 6 | O | O | $CH_3$ | tetrahydrofuran-3-yl | 2-(SCH$_3$)phenyl | 185 |
| 7 | O | O | $CH_3$ | tetrahydrofuran-3-yl | 2-(OCHF$_2$)phenyl | 167 |
| 8 | O | O | $CH_3$ | tetrahydrofuran-3-yl | 2-(COOCH$_3$)phenyl | 143 |
| 9 | O | O | $CH_3$ | tetrahydrofuran-3-yl | 2-(CF$_3$)phenyl | 181 |
| 10 | O | O | cyclopropylmethyl | tetrahydrofuran-3-yl | 2-(CF$_3$)phenyl | 200 |
| 11 | O | O | $CH_3$ | oxetan-3-yl | 2-(COOCH$_3$)phenyl | |
| 12 | O | O | $CH_3$ | oxetan-3-yl | 2-(OC$_2$H$_5$)phenyl | |

TABLE 1-continued
Examples of the compounds of the formula (I)
| Ex. No. | Q¹ | Q² | R¹ | R² | R³ | Melting point (° C.) |
|---|---|---|---|---|---|---|
| 13 | O | O | CH₃ |  | 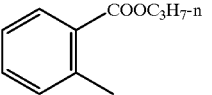 COOC₃H₇-n | |
| 14 | O | O | CH₃ |  | 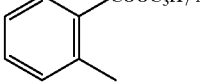 COOC₃H₇-I | |
| 15 | O | O | CH₃ |  | 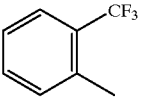 CF₃ | |
| 16 | O | O | CH₃ |  | 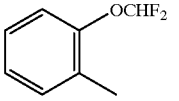 OCHF₂ | |
| 17 | O | O | CH₃ |  | 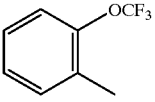 OCF₃ | |
| 18 | O | O | CH₃ |  | 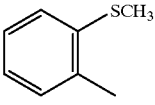 SCH₃ | |
| 19 | O | O | CH₃ |  | 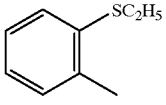 SC₂H₅ | |
| 20 | O | O | CH₃ |  | 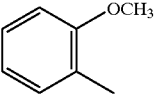 OCH₃ | |
| 21 | O | O | CH₃ |  | 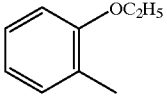 OC₂H₅ | |
| 22 | O | O | CH₃ |  | 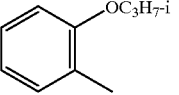 OC₃H₇-i | |

TABLE 1-continued
Examples of the compounds of the formula (I)
| Ex. No. | Q¹ | Q² | R¹ | R² | R³ | Melting point (° C.) |
|---|---|---|---|---|---|---|
| 23 | O | O | CH₃ |  | 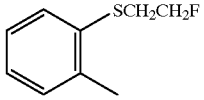 | |
| 24 | O | O | CH₃ |  | 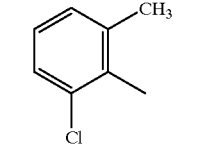 | |
| 25 | O | O | CH₃ |  | 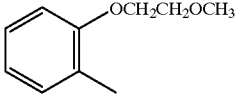 | |
| 26 | O | O | CH₃ |  | 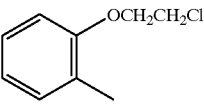 | |
| 27 | O | O | CH₃ |  | 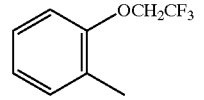 | |
| 28 | O | O | CH₃ |  | 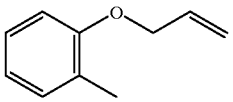 | |
| 29 | O | O | CH₃ |  | 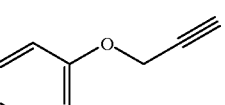 | |
| 30 | O | O |  |  | 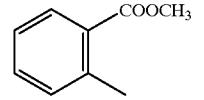 | |
| 31 | O | O |  |  | 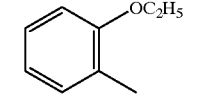 | |
| 32 | O | O |  |  | 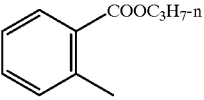 | |

TABLE 1-continued

Examples of the compounds of the formula (I)

| Ex. No. | Q¹ | Q² | R¹ | R² | R³ | Melting point (° C.) |
|---|---|---|---|---|---|---|
| 33 | O | O | cyclopropyl | oxetanyl | 2-methylphenyl with COOC$_3$H$_7$-i | |
| 34 | O | O | cyclopropyl | oxetanyl | 2-methylphenyl with CF$_3$ | 103 |
| 35 | O | O | cyclopropyl | oxetanyl | 2-methylphenyl with OCHF$_2$ | |
| 36 | O | O | cyclopropyl | oxetanyl | 2-methylphenyl with OCF$_3$ | |
| 37 | O | O | cyclopropyl | oxetanyl | 2-methylphenyl with SCH$_3$ | |
| 38 | O | O | cyclopropyl | oxetanyl | 2-methylphenyl with SC$_2$H$_5$ | |
| 39 | O | O | cyclopropyl | oxetanyl | 2-methylphenyl with OCH$_3$ | |
| 40 | O | O | cyclopropyl | oxetanyl | 2-methylphenyl with OC$_2$H$_5$ | |
| 41 | O | O | cyclopropyl | oxetanyl | 2-methylphenyl with OC$_3$H$_7$-i | |
| 42 | O | O | cyclopropyl | oxetanyl | 2-methylphenyl with SCH$_2$CH$_2$F | |
| 43 | O | O | cyclopropyl | oxetanyl | 2-methyl-3-chlorophenyl | |

TABLE 1-continued

Examples of the compounds of the formula (I)

| Ex. No. | Q¹ | Q² | R¹ | R² | R³ | Melting point (° C.) |
|---------|----|----|----|----|----|----------------------|
| 44 | O | O | cyclopropyl | oxetanyl | 2-methylphenyl-OCH₂CH₂OCH₃ | |
| 45 | O | O | cyclopropyl | oxetanyl | 2-methylphenyl-OCH₂CH₂Cl | |
| 46 | O | O | cyclopropyl | oxetanyl | 2-methylphenyl-OCH₂CF₃ | |
| 47 | O | O | cyclopropyl | oxetanyl | 2-methylphenyl-O-allyl | |
| 48 | O | O | cyclopropyl | oxetanyl | 2-methylphenyl-O-propargyl | |
| 49 | O | O | cyclopropylmethyl | oxetanyl | 2-methylphenyl-COOCH₃ | |
| 50 | O | O | cyclopropylmethyl | oxetanyl | 2-methylphenyl-OC₂H₅ | |
| 51 | O | O | cyclopropylmethyl | oxetanyl | 2-methylphenyl-OC₂H₅ | |
| 52 | O | O | cyclopropylmethyl | oxetanyl | 2-methylphenyl-COOC₃H₇-i | |
| 53 | O | O | cyclopropylmethyl | oxetanyl | 2-methylphenyl-CF₃ | |
| 54 | O | O | cyclopropylmethyl | oxetanyl | 2-methylphenyl-OCHF₂ | |
| 55 | O | O | cyclopropylmethyl | oxetanyl | 2-methylphenyl-OCF₃ | |

TABLE 1-continued

Examples of the compounds of the formula (I)

| Ex. No. | Q¹ | Q² | R¹ | R² | R³ | Melting point (° C.) |
|---|---|---|---|---|---|---|
| 56 | O | O | -CH₂-cyclopropyl | 3-oxetanyl | 2-methyl-6-(SCH₃)phenyl | |
| 57 | O | O | -CH₂-cyclopropyl | 3-oxetanyl | 2-methyl-6-(SC₂H₅)phenyl | |
| 58 | O | O | -CH₂-cyclopropyl | 3-oxetanyl | 2-methyl-6-(OCH₃)phenyl | |
| 59 | O | O | -CH₂-cyclopropyl | 3-oxetanyl | 2-methyl-6-(OC₂H₅)phenyl | |
| 60 | O | O | -CH₂-cyclopropyl | 3-oxetanyl | 2-methyl-6-(OC₃H₇-i)phenyl | |
| 61 | O | O | -CH₂-cyclopropyl | 3-oxetanyl | 2-methyl-6-(SCH₂CH₂F)phenyl | |
| 62 | O | O | -CH₂-cyclopropyl | 3-oxetanyl | 2-methyl-3-CH₃-6-Cl-phenyl | |
| 63 | O | O | -CH₂-cyclopropyl | 3-oxetanyl | 2-methyl-6-(OCH₂CH₂OCH₃)phenyl | |
| 64 | O | O | -CH₂-cyclopropyl | 3-oxetanyl | 2-methyl-6-(OCH₂CH₂Cl)phenyl | |
| 65 | O | O | -CH₂-cyclopropyl | 3-oxetanyl | 2-methyl-6-(OCH₂CF₃)phenyl | |
| 66 | O | O | -CH₂-cyclopropyl | 3-oxetanyl | 2-methyl-6-(O-allyl)phenyl | |

TABLE 1-continued

Examples of the compounds of the formula (I)

| Ex. No. | Q¹ | Q² | R¹ | R² | R³ | Melting point (° C.) |
|---|---|---|---|---|---|---|
| 67 | O | O | -CH2-cyclopropyl | 3-oxetanyl | 2-methyl-6-(prop-2-ynyloxy)phenyl | |
| 68 | O | O | allyl | 3-oxetanyl | 2-methyl-6-(COOCH3)phenyl | |
| 69 | O | O | allyl | 3-oxetanyl | 2-methyl-6-(OC2H5)phenyl | |
| 70 | O | O | allyl | 3-oxetanyl | 2-methyl-6-(COOC3H7-n)phenyl | |
| 71 | O | O | allyl | 3-oxetanyl | 2-methyl-6-(COOC3H7-i)phenyl | |
| 72 | O | O | allyl | 3-oxetanyl | 2-methyl-6-(CF3)phenyl | |
| 73 | O | O | allyl | 3-oxetanyl | 2-methyl-6-(OCHF2)phenyl | |
| 74 | O | O | allyl | 3-oxetanyl | 2-methyl-6-(OCF3)phenyl | |
| 75 | O | O | allyl | 3-oxetanyl | 2-methyl-6-(SCH3)phenyl | |
| 76 | O | O | allyl | 3-oxetanyl | 2-methyl-6-(SC2H5)phenyl | |
| 77 | O | O | allyl | 3-oxetanyl | 2-methyl-6-(OCH3)phenyl | |
| 78 | O | O | allyl | 3-oxetanyl | 2-methyl-6-(OC2H5)phenyl | |

TABLE 1-continued

Examples of the compounds of the formula (I)

| Ex. No. | Q¹ | Q² | R¹ | R² | R³ | Melting point (° C.) |
|---|---|---|---|---|---|---|
| 79 | O | O | CH₂CH=CH₂ | oxetanyl | 2-methyl-6-(OC₃H₇-i)phenyl | |
| 80 | O | O | CH₂CH=CH₂ | oxetanyl | 2-methyl-6-(SCH₂CH₂F)phenyl | |
| 81 | O | O | CH₂CH=CH₂ | oxetanyl | 2,3-dimethyl-6-Cl-phenyl | |
| 82 | O | O | CH₂CH=CH₂ | oxetanyl | 2-methyl-6-(OCH₂CH₂OCH₃)phenyl | |
| 83 | O | O | CH₂CH=CH₂ | oxetanyl | 2-methyl-6-(OCH₂CH₂Cl)phenyl | |
| 84 | O | O | CH₂CH=CH₂ | oxetanyl | 2-methyl-6-(OCH₂CF₃)phenyl | |
| 85 | O | O | CH₂CH=CH₂ | oxetanyl | 2-methyl-6-(OCH₂CH=CH₂)phenyl | |
| 86 | O | O | CH₂CH=CH₂ | oxetanyl | 2-methyl-6-(OCH₂C≡CH)phenyl | |
| 87 | O | O | OCH₃ | oxetanyl | 2-methyl-6-(COOCH₃)phenyl | |
| 88 | O | O | OCH₃ | oxetanyl | 2-methyl-6-(OC₂H₅)phenyl | |
| 89 | O | O | OCH₃ | oxetanyl | 2-methyl-6-(COOC₃H₇-n)phenyl | |

TABLE 1-continued
Examples of the compounds of the formula (I)
| Ex. No. | Q¹ | Q² | R¹ | R² | R³ | Melting point (° C.) |
|---|---|---|---|---|---|---|
| 90 | O | O | OCH$_3$ |  | 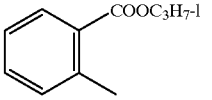 | |
| 91 | O | O | OCH$_3$ |  | 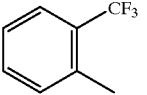 | |
| 92 | O | O | OCH$_3$ |  | 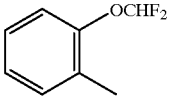 | |
| 93 | O | O | OCH$_3$ |  | 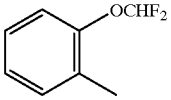 | |
| 94 | O | O | OCH$_3$ |  | 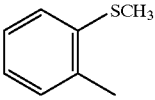 | |
| 95 | O | O | OCH$_3$ |  | 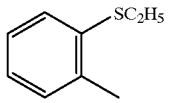 | |
| 96 | O | O | OCH$_3$ |  | 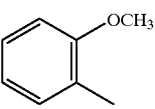 | |
| 97 | O | O | OCH$_3$ |  | 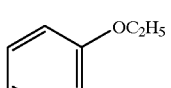 | |
| 98 | O | O | OCH$_3$ |  | 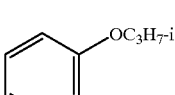 | |
| 99 | O | O | OCH$_3$ |  | 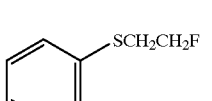 | |

TABLE 1-continued
Examples of the compounds of the formula (I)
| Ex. No. | Q¹ | Q² | R¹ | R² | R³ | Melting point (° C.) |
|---|---|---|---|---|---|---|
| 100 | O | O | OCH₃ |  | 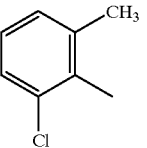 | |
| 101 | O | O | OCH₃ |  | 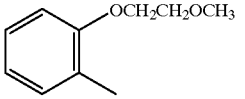 | |
| 102 | O | O | OCH₃ |  | 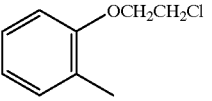 | |
| 103 | O | O | OCH₃ |  | 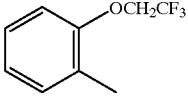 | |
| 104 | O | O | OCH₃ |  | 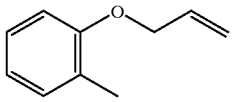 | |
| 105 | O | O | OCH₃ |  | 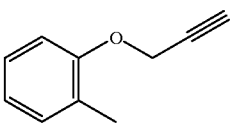 | |
| 106 | O | O | OC₂H₅ |  | 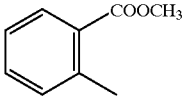 | |
| 107 | O | O | OC₂H₅ |  | 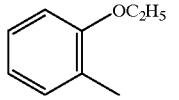 | |
| 108 | O | O | OC₂H₅ |  | 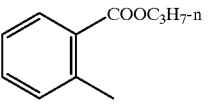 | |
| 109 | O | O | OC₂H₅ |  | 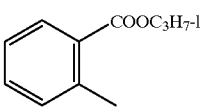 | |

TABLE 1-continued

Examples of the compounds of the formula (I)

| Ex. No. | Q¹ | Q² | R¹ | R² | R³ | Melting point (° C.) |
|---|---|---|---|---|---|---|
| 110 | O | O | OC$_2$H$_5$ | oxetan-3-yl | 2-(CF$_3$)phenyl | |
| 111 | O | O | OC$_2$H$_5$ | oxetan-3-yl | 2-(OCHF$_2$)phenyl | |
| 112 | O | O | OC$_2$H$_5$ | oxetan-3-yl | 2-(OCF$_3$)phenyl | |
| 113 | O | O | OCH$_3$ | oxetan-3-yl | 2-(SCH$_3$)phenyl | |
| 114 | O | O | OC$_2$H$_5$ | oxetan-3-yl | 2-(SC$_2$H$_5$)phenyl | |
| 115 | O | O | OC$_2$H$_5$ | oxetan-3-yl | 2-(OCH$_3$)phenyl | |
| 116 | O | O | OC$_2$H$_5$ | oxetan-3-yl | 2-(OC$_2$H$_5$)phenyl | |
| 117 | O | O | OC$_2$H$_5$ | oxetan-3-yl | 2-(OC$_3$H$_7$-i)phenyl | |
| 118 | O | O | OC$_2$H$_5$ | oxetan-3-yl | 2-(SCH$_2$CH$_2$F)phenyl | |
| 119 | O | O | OC$_2$H$_5$ | oxetan-3-yl | 2-CH$_3$-3-Cl-phenyl | |

TABLE 1-continued

Examples of the compounds of the formula (I)

| Ex. No. | Q¹ | Q² | R¹ | R² | R³ | Melting point (° C.) |
|---|---|---|---|---|---|---|
| 120 | O | O | OC₂H₅ |  | 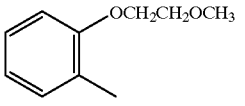 | |
| 121 | O | O | OCH₃ |  | 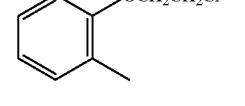 | |
| 122 | O | O | OC₂H₅ |  | 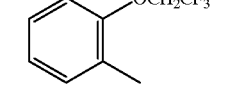 | |
| 123 | O | O | OC₂H₅ |  | 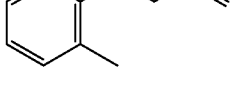 | |
| 124 | O | O | OC₂H₅ |  | 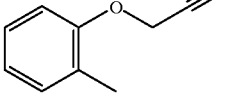 | |

Starting Materials of the Formula (II):

Example (II-1)

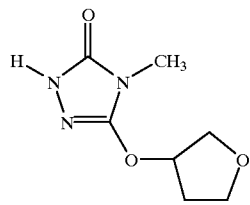

Step 1:

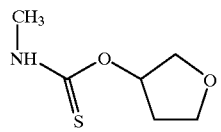

233 g (2.65 mol) of 3-hydroxy-tetrahydrofuran are azeotropically dewatered in 750 ml toluene under a water pump vacuum at 50 mbar. Then, with ice cooling, 18 g (0.60 mol) of sodium hydride (80% pure) are added over the course of about 20 minutes. After 30 minutes, 176 g (2.41 mol) of methyl isothiocyanate are added dropwise over the course of about 30 minutes at 50° C., with ice cooling. The reaction mixture is then stirred at 50° C. for about 2 hours more. It is subsequently neutralized with 71.2 g of 30.7% strength hydrochloric acid (0.60 mol of HCl), with ice cooling, and finally is azeotropically dewatered at 100 mbar and filtered, and the filtrate is concentrated to about 500 g.

Step 2:

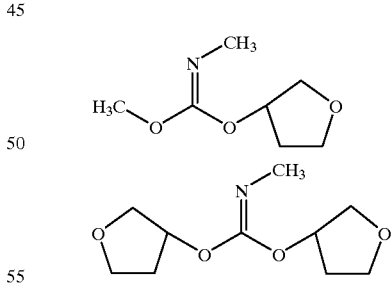

782 g (2.65 mol) of dibutyltin dimethoxide are initially introduced at 40° C. under an oil pump vacuum, and the product solution obtained in step 1 is added dropwise over the course of about 30 minutes. During this addition, methanol is distilled off and the temperature is raised to about 80° C. Subsequently, the air is replaced by nitrogen and the reaction mixture is stirred at 100° C. for 16 hours. It is then rectified under an oil pump vacuum. Following the distillation of an initial fraction of 43 g, 290 ml of main fraction are obtained (at 1 mbar/60° C.), which according to analysis by gas chromatography consist of 203.5 g (1.28 mol) of methylimino-carbonic acid O-methyl ester O-(3-tetrahydrofuryl) ester and 75.2 g (0.35 mol) of methylimino-carbonic acid O,O-bis(3-tetrahydrofuryl) ester.

Step 3:

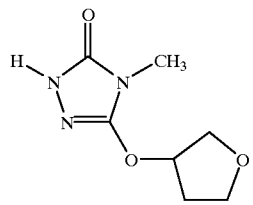

261 g (1.63 mol) of 2-ethoxyethyl carbazinate are initially introduced at 0° C. and the product mixture from step 2, which has been cooled to 0° C., is added all at once. Then 1.66 g portions of pivalic acid are added at intervals of about 20 minutes and the mixture is stirred at 20° C. for 16 hours and then at 45° C. for 30 minutes more. Following the addition of 299 g of 30% strength methanol sodium methylate solution (1.66 mol sodium methylate), the mixture is stirred at 55° C. for a further 3 hours. After it has cooled, the reaction mixture is neutralized with 197 g of 30.7% strength hydrochloric acid (1.66 mol of HCl), with ice cooling, and then concentrated under a water pump vacuum. The residue is recrystallized from 750 ml of toluene, to give 209 g of a product mixture which, according to analysis by gas chromatography, consists to the extent of 51% of 4-methyl-5-methoxy-2,4-dihydro-3H-1,2,4-triazol-3-one and to the extent of 43% of 4-methyl-5-(3-tetrahydrofuryl-oxy)-2,4-dihydro-3H-1,2,4-triazol-3-one. The product mixture is recrystallized from 400 ml of water, giving 50 g of 4-methyl-5-methoxy-2,4-dihydro-3H-1,2,4-triazol-3-one as a crystalline product. The mother liquor is concentrated by evaporation and the residue is recrystallized from 400 ml of toluene. Renewed recrystallization of the product from methanol gives 83 g (0.45 mol) of 4-methyl-5-(3-tetrahydrofuryl-oxy)-2,4-dihydro-3H- 1,2,4-triazol-3-one of melting point 164° C.

In analogy to Example (II-1) it is also possible, for example, to prepare the compounds of the formula (II) which are listed in Table 2 below.

(II)

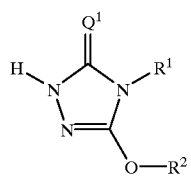

TABLE 2

Examples of the compounds of the formula (II)

| Ex. No. | Q¹ | R¹ | R² | Melting point (° C.) |
|---|---|---|---|---|
| II-2 | O | CH₃ | thietan-3-yl | |
| II-3 | O | CH₃ | oxetan-3-yl | |
| II-4 | O | CH₃ | (thietan-3-yl)methyl | |
| II-5 | O | CH₃ | (oxetan-3-yl)methyl | |
| II-6 | O | CH₃ | (tetrahydrofuran-2-yl)methyl | |
| II-7 | O | cyclopropyl | thietan-3-yl | |
| II-8 | O | cyclopropyl | oxetan-3-yl | |
| II-9 | O | cyclopropyl | (thietan-3-yl)methyl | |
| II-10 | O | cyclopropyl | (oxetan-3-yl)methyl | |
| II-11 | O | cyclopropyl | (tetrahydrofuran-2-yl)methyl | |
| II-12 | O | cyclopropylmethyl | thietan-3-yl | |
| II-13 | O | cyclopropylmethyl | oxetan-3-yl | |
| II-14 | O | cyclopropylmethyl | (thietan-3-yl)methyl | |

TABLE 2-continued

Examples of the compounds of the formula (II)

| Ex. No. | Q¹ | R¹ | R² | Melting point (° C.) |
|---|---|---|---|---|
| II-15 | O | cyclopropylmethyl | oxetanylmethyl (O) | |
| II-16 | O | cyclopropylmethyl | tetrahydrofuranylmethyl | |
| II-17 | O | allyl | thietanyl (S) | |
| II-18 | O | allyl | oxetanyl (O) | |
| II-19 | O | allyl | thietanylmethyl (S) | |
| II-20 | O | allyl | oxetanylmethyl (O) | |
| II-21 | O | allyl | tetrahydrofuranylmethyl | |
| II-22 | O | OCH₃ | thietanyl (S) | |
| II-23 | O | OCH₃ | oxetanyl (O) | |
| II-24 | O | OCH₃ | thietanylmethyl (S) | |
| II-25 | O | OCH₃ | oxetanylmethyl (O) | |
| II-26 | O | OCH₃ | tetrahydrofuranylmethyl | |
| II-27 | O | OC₂H₅ | thietanyl (S) | |
| II-28 | O | OC₂H₅ | oxetanyl (O) | |
| II-29 | O | OC₂H₅ | thietanylmethyl (S) | |
| II-30 | O | OC₂H₅ | oxetanylmethyl (O) | |
| II-31 | O | OC₂H₅ | tetrahydrofuranylmethyl | |
| II-32 | O | N(CH₃)₂ | thietanyl (S) | |
| II-33 | O | N(CH₃)₂ | oxetanyl (O) | |
| II-34 | O | N(CH₃)₂ | thietanylmethyl (S) | |
| II-35 | O | N(CH₃)₂ | oxetanylmethyl (O) | |
| II-36 | O | N(CH₃)₂ | tetrahydrofuranylmethyl | |

Starting Materials of the Formula (IV):

Example (IV-1)

6.9 g (44 mmol) of phenyl chloroformate are added dropwise with stirring at from 20° C. to 30° C. to a mixture of 7.4 g (40 mmol) of 4-methyl-5-(3-tetrahydrofuryloxy)-2,4-dihydro-3H-1,2,4-triazol-3-one, 1.8 g (44 mmol) of sodium hydroxide, 0.2 g of tetrabutylammonium chloride, 50 ml of water and 50 ml of methylene chloride, and the reaction mixture is stirred at 20° C. for 12 hours. The organic phase is subsequently separated off, washed with water, dried over sodium sulphate and filtered. The filtrate is concentrated under a water pump vacuum, the residue is digested with petroleum ether, and the crystalline product obtained in this procedure is isolated by filtration with suction.

11.8 g (97% of theory) of 4-methyl-2-phenoxycarbonyl-5-(3-tetrahydrofuryloxy)-2,4-dihydro-3H-1,2,4-triazol-3-one are obtained of melting point 98° C.

In analogy to Example (IV-1) it is also possible, for example, to prepare the compounds of the formula (IV) which are listed in Table 3 below.

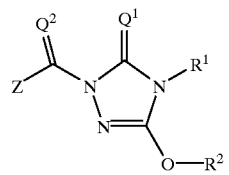

(IV)

TABLE 3

| | | Examples of the compounds of the formula (IV) | | | | |
|---|---|---|---|---|---|---|
| Ex. No. | $Q^1$ | $Q^2$ | $R^1$ | $R^2$ | Z | Melting point (° C.) |
| IV-2 | S | O | $CH_3$ | 3-tetrahydrofuryl | $OC_6H_5$ | |
| IV-3 | O | O | $CH_3$ | 3-oxetanyl | $OC_6H_5$ | |
| IV-4 | O | O | $CH_3$ | 3-oxetanyl | Cl | |
| IV-5 | S | O | $CH_3$ | 3-oxetanyl | $OC_6H_5$ | |
| IV-6 | S | O | $CH_3$ | 3-oxetanyl | Cl | |
| IV-7 | O | O | $CH_3$ | 3-thietanyl | $OC_6H_5$ | |
| IV-8 | O | O | $CH_3$ | 3-oxetanylmethyl | $OC_6H_5$ | |
| IV-9 | O | O | $CH_3$ | tetrahydrofuran-2-ylmethyl | $OC_6H_5$ | |

TABLE 3-continued

Examples of the compounds of the formula (IV)

| Ex. No. | $Q^1$ | $Q^2$ | $R^1$ | $R^2$ | Z | Melting point (° C.) |
|---------|-------|-------|-------|-------|---|----------------------|
| IV-10 | S | O | cyclopropyl | tetrahydrofuran-3-yl | $OC_6H_5$ | |
| IV-11 | O | O | cyclopropyl | oxetan-3-yl | $OC_6H_5$ | |
| IV-12 | O | O | cyclopropyl | oxetan-3-yl | Cl | |
| IV-13 | S | O | cyclopropyl | oxetan-3-yl | $OC_6H_5$ | |
| IV-14 | S | O | cyclopropyl | oxetan-3-yl | Cl | |
| IV-15 | O | O | cyclopropyl | thietan-3-yl | $OC_6H_5$ | |
| IV-16 | O | O | cyclopropyl | (oxetan-3-yl)methyl | $OC_6H_5$ | |
| IV-17 | O | O | cyclopropyl | (tetrahydrofuran-2-yl)methyl | $OC_6H_5$ | |
| IV-18 | S | O | $C_2H_5$ | tetrahydrofuran-3-yl | $OC_6H_5$ | |
| IV-19 | O | O | $C_2H_5$ | oxetan-3-yl | $OC_6H_5$ | |
| IV-20 | O | O | $C_2H_5$ | oxetan-3-yl | Cl | |
| IV-21 | S | O | $C_2H_5$ | oxetan-3-yl | $OC_6H_5$ | |
| IV-22 | S | O | $C_2H_5$ | oxetan-3-yl | Cl | |

TABLE 3-continued

Examples of the compounds of the formula (IV)

| Ex. No. | Q¹ | Q² | R¹ | R² | Z | Melting point (° C.) |
|---|---|---|---|---|---|---|
| IV-23 | O | O | $C_2H_5$ | (3-thietanylmethyl) | $OC_6H_5$ | |
| IV-24 | O | O | $C_2H_5$ | (3-oxetanylmethyl) | $OC_6H_5$ | |
| IV-25 | O | O | $C_2H_5$ | (tetrahydrofuran-2-ylmethyl) | $OC_6H_5$ | |
| IV-26 | S | O | allyl | (tetrahydrofuran-3-ylmethyl) | $OC_6H_5$ | |
| IV-27 | O | O | allyl | (3-oxetanylmethyl) | $OC_6H_5$ | |
| IV-28 | O | O | allyl | (3-oxetanylmethyl) | Cl | |
| IV-29 | S | O | allyl | (3-oxetanylmethyl) | $OC_6H_5$ | |
| IV-30 | S | O | allyl | (3-oxetanylmethyl) | Cl | |
| IV-31 | O | O | allyl | (3-thietanylmethyl) | $OC_6H_5$ | |
| IV-32 | O | O | allyl | (3-oxetanylmethyl) | $OC_6H_5$ | |
| IV-33 | O | O | allyl | (tetrahydrofuran-2-ylmethyl) | $OC_6H_5$ | |
| IV-34 | S | O | $N(CH_3)_2$ | (tetrahydrofuran-3-ylmethyl) | $OC_6H_5$ | |
| IV-35 | O | O | $N(CH_3)_2$ | (3-oxetanylmethyl) | $OC_6H_5$ | |

TABLE 3-continued

Examples of the compounds of the formula (IV)

| Ex. No. | Q¹ | Q² | R¹ | R² | Z | Melting point (° C.) |
|---|---|---|---|---|---|---|
| IV-36 | O | O | N(CH$_3$)$_2$ | oxetan-3-yl (O) | Cl | |
| IV-37 | S | O | N(CH$_3$)$_2$ | oxetan-3-yl (O) | OC$_6$H$_5$ | |
| IV-38 | S | O | N(CH$_3$)$_2$ | oxetan-3-yl (O) | Cl | |
| IV-39 | O | O | N(CH$_3$)$_2$ | thietan-3-yl (S) | OC$_6$H$_5$ | |
| IV-40 | O | O | N(CH$_3$)$_2$ | (oxetan-3-yl)methyl | OC$_6$H$_5$ | |
| IV-41 | O | O | N(CH$_3$)$_2$ | (tetrahydrofuran-2-yl)methyl | OC$_6$H$_5$ | |
| IV-42 | S | O | OCH$_3$ | tetrahydrofuran-3-yl | OC$_6$H$_5$ | |
| IV-43 | O | O | OCH$_3$ | oxetan-3-yl | OC$_6$H$_5$ | |
| IV-44 | O | O | OCH$_3$ | oxetan-3-yl | Cl | |
| IV-45 | S | O | OCH$_3$ | oxetan-3-yl | OC$_6$H$_5$ | |
| IV-46 | S | O | OCH$_3$ | oxetan-3-yl | Cl | |
| IV-47 | O | O | OCH$_3$ | thietan-3-yl | OC$_6$H$_5$ | |

TABLE 3-continued
Examples of the compounds of the formula (IV)
| Ex. No. | Q¹ | Q² | R¹ | R² | Z | Melting point (° C.) |
|---------|----|----|-----|-----|-----|-----|
| IV-48 | O | O | OCH$_3$ | 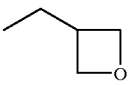 | OC$_6$H$_5$ | |
| IV-49 | O | O | OCH$_3$ | 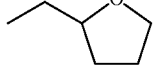 | OC$_6$H$_5$ | |
| IV-50 | S | O | OC$_2$H$_5$ | 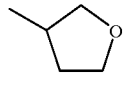 | OC$_6$H$_5$ | |
| IV-51 | O | O | OC$_2$H$_5$ |  | OC$_6$H$_5$ | |
| IV-52 | O | O | OC$_2$H$_5$ |  | Cl | |
| IV-53 | S | O | OC$_2$H$_5$ |  | OC$_6$H$_5$ | |
| IV-54 | S | O | OC$_2$H$_5$ |  | Cl | |
| IV-55 | O | O | OC$_2$H$_5$ |  | OC$_6$H$_5$ | |
| IV-56 | O | O | OC$_2$H$_5$ |  | OC$_6$H$_5$ | |
| IV-57 | O | O | OC$_2$H$_5$ | 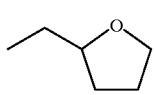 | OC$_6$H$_5$ | |
| IV-58 | S | O | 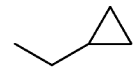 | 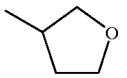 | OC$_6$H$_5$ | |
| IV-59 | O | O | 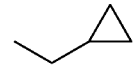 |  | OC$_6$H$_5$ | |

TABLE 3-continued

Examples of the compounds of the formula (IV)

| Ex. No. | $Q^1$ | $Q^2$ | $R^1$ | $R^2$ | Z | Melting point (° C.) |
|---|---|---|---|---|---|---|
| IV-60 | O | O | cyclopropylmethyl | oxetanyl | Cl | |
| IV-61 | S | O | cyclopropylmethyl | oxetanyl | $OC_6H_5$ | |
| IV-62 | S | O | cyclopropylmethyl | oxetanyl | Cl | |
| IV-63 | O | O | cyclopropylmethyl | thietanyl | $OC_6H_5$ | |
| IV-64 | O | O | cyclopropylmethyl | oxetanylmethyl | $OC_6H_5$ | |
| IV-65 | O | O | cyclopropylmethyl | tetrahydrofuranylmethyl | $OC_6H_5$ | |

Use Examples

Example A

Pre-emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after about 24 hours, the soil is watered with the preparation of the active compound. It is expedient to keep constant the amount of water per unit area. The concentration of the active compound in the preparation is of no importance, only the amount of active compound applied per unit area being decisive.

After three weeks, the degree of damage to the plants is rated in % damage in comparison to the development of the untreated control.

The figures denote:

0%=no action (like untreated control)

100%=total destruction

In this test, the compounds of the formula (I) according to the invention exhibit a strong action against weeds (see Table A).

Example B

Post-emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 1,000 l of water/ha.

After three weeks, the degree of damage to the plants is rated in % damage in comparison to the development of the untreated control.

The figures denote:

0%=no action (like untreated control)

100%=total destruction

In this test, the compounds of the formula (I) according to the invention exhibit a strong action against weeds (see Table B).

TABLE A

Pre-emergence test/greenhouse

| Active Compound according to Example No. | g ai./ha | Alopecurus | Bromus | Cyperus | Lolium | Amaranthus | Cassia | Chenopodium | Veronica |
|---|---|---|---|---|---|---|---|---|---|
| (34) | 500 | 100 | 100 | 100 | 100 | 100 | 100 | 100 | 100 |

[see Table 1]

TABLE B

Post-emergence test/greenhouse

| Active Compound according to Example No. | g ai./ha | Amaranthus | Solanum | Stellaria | Xanthium |
|---|---|---|---|---|---|
| (34) | 500 | 95 | 95 | 90 | 95 |

[See Table 1]

We claim:

1. A compound of the formula (I)

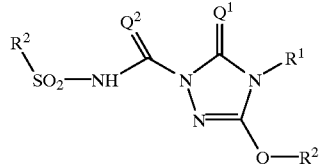

(I)

wherein

Q$^1$ represents oxygen or sulphur,

Q$^2$ represents oxygen or sulphur,

R$^1$ represents hydrogen, hydroxyl, amino or C$_1$–C$_6$-alkylideneamino, or represents optionally fluoro-, chloro-, bromo-, cyano-, C$_1$–C$_4$-alkoxy-, C$_1$–C$_4$-alkylcarbonyl- or C$_1$–C$_4$-alkoxy-cabonyl-substituted C$_1$–C$_6$-alkyl, or represents in each case optionally fluoro-, chloro- and/or bromo-substituted C$_2$–C$_6$-alkenyl or C$_2$–C$_6$-alkinyl, or represents C$_1$–C$_6$-alkyloxy or C$_3$–C$_6$-alkenyloxy, or represents in each case optionally fluoro- and/or chloro-substituted C$_1$–C$_6$-alkylamino, di-(C$_1$–C$_4$-alkyl)-amino or C$_1$–C$_4$-alkanoylamino, or represents in each case optionally fluoro-, chloro-, bromo- and/or C$_1$–C$_4$-alkyl-substituted C$_3$–C$_6$-cycloalkyl or C$_3$–C$_6$-cycloalkyl-C$_1$–C$_4$-alkyl, or represents in each case optionally fluoro-, chloro-, bromo-, cyano-, nitro-, C$_1$–C$_4$-alkyl-, trifluoromethyl-, C$_1$–C$_4$-alkoxy- and/or C$_1$–C$_4$-alkoxycarbonyl-substituted phenyl or phenyl-C$_1$–C$_4$-alkyl, R$^2$ represents in each case optionally halogeno- and/or C$_1$–C$_4$-alkyl substituted oxetanyl, thietanyl, furyl, tetrahydrofuryl, thienyl, tetrahydrothienyl, oxetanyl-C$_1$–C$_4$-alkyl, thietanyl-C$_1$–C$_4$-alkyl, furyl-C$_1$–C$_4$-alkyl, tetrahydrofuryl-C$_1$–C$_4$-alkyl, thienyl-C$_1$–C$_4$-alkyl, tetrahydrothienyl-C$_1$–C$_4$-alkyl, and R$^3$ represents the group

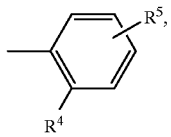

in which

R$^4$ and R$^5$ are identical or different and represent hydrogen, fluoro, chloro, bromo, iodo, nitro or C$_1$–C$_6$-alkyl (which is optionally substituted by fluoro, chloro, bromo, cyano, carboxyl, C$_1$–C$_4$-alkoxycarbonyl, C$_1$–C$_4$-alkylamino-carbonyl, di-(C$_1$–C$_4$-alkyl)-amino-carbonyl, hydroxyl, C$_1$–C$_4$-alkoxy, formyloxy, C$_1$–C$_4$-alkyl-carbonyloxy, C$_1$–C$_4$-alkylamino-carbonyloxy, C$_1$–C$_4$-alkylthio, C$_1$–C$_4$-alkylsulphinyl, C$_1$–C$_4$-alkylsulphonyl, di-(C$_1$–C$_4$-alkyl)-amino-sulphonyl, C$_3$–C$_6$-cycloalkyl or phenyl), or represent C$_2$–C$_6$-alkenyl (which is optionally substituted by fluoro, chloro, bromo, cyano, C$_1$–C$_4$-alkoxy-carbonyl, carboxyl or phenyl), or represent C$_2$–C$_6$alkinyl (which is optionally substituted by fluoro, chloro, bromo, cyano, C$_1$–C$_4$-alkoxy-carbonyl, carboxyl or phenyl), or represent C$_1$–C$_4$-alkoxy (which is optionally substituted by fluoro, chloro, bromo, cyano, carboxyl, C$_1$–C$_4$-alkoxy-carbonyl, C$_1$–C$_4$-alkoxy, C$_1$–C$_4$-alkylthio, C$_1$–C$_4$-alkylsulphinyl or C$_1$–C$_4$-alkylsulphonyl), or represent C$_1$–C$_4$-alkylthio (which is optionally substituted by fluoro, chloro, bromo, cyano, carboxyl, C$_1$–C$_4$-alkoxy-carbonyl, C$_1$–C$_4$-alkylthio, C$_1$–C$_4$-alkylsulphinyl or C$_1$–C$_4$-alkylsulphonyl), or represent C$_2$–C$_6$-alkenyloxy (which is optionally substituted by fluoro, chloro, bromo, cyano or C$_1$–C$_4$-alkoxy-carbonyl), or represent C$_2$–C$_6$-alkenylthio (which is optionally substituted by fluoro, chloro, bromo, cyano, nitro, C$_1$–C$_3$-alkylthio or C$_1$–C$_4$-alkoxy-carbonyl), C$_3$–C$_6$-alkinyloxy or C$_3$–C$_6$-alkinylthio, or represent the radical —S(O)$_p$-R$^6$, where p represents the numbers 1 or 2 and R$^6$ represents C$_1$–C$_4$-alkyl (which is optionally substituted by fluoro, chloro, bromo, cyano or C$_1$–C$_4$-alkoxy-carbonyl), C$_3$–C$_6$-alkenyl, C$_3$–C$_6$-alkinyl, C$_1$–C$_4$-alkoxy, C$_1$–C$_4$-alkoxy-C$_1$–C$_4$-alkylamino, C$_1$–C$_4$-alkylamino, di-(C$_1$–C$_4$-alkyl)-amino or phenyl or represents the radical —NHR$^7$, where R$^7$ represents C$_1$–C$_{12}$-alkyl (which is optionally substituted by fluoro, chloro, cyano, C$_1$–C$_4$-alkoxy, C$_1$–C$_4$-alkylthio, C$_1$–C$_4$-alkylsulphinyl, C$_1$–C$_4$-alkylsulphonyl, C$_1$–C$_4$-alkyl-carbonyl, C$_1$–C$_4$-alkoxy-carbonyl, C$_1$–C$_4$-alkylaminocarbonyl or Di-(C$_1$–C$_4$-alkyl)-amino-carbonyl), or represents C$_3$–C$_6$-alkenyl (which is optionally substituted by fluoro, chloro or bromo), $C_3$–$C_6$-alkinyl, $C_3$–$C_6$-cycloalkyl, $C_3$–$C_6$-cycloalkyl-$C_1$–$C_2$-alkyl or phenyl-$C_1$–$C_2$-alkyl (which is optionally substituted by fluoro, chloro, nitro, cyano, $C_1$–$C_4$-alkyl, $C_1$–$C_4$-alkoxy or $C_1$–$C_4$-alkoxy-carbonyl), or represents benzhydryl or represents phenyl (which is optionally substituted by fluoro, chloro, nitro, cyano, $C_1$–$C_4$-alkyl, trifluoromethyl, $C_1$–$C_4$-alkoxy, $C_1$–$C_2$-fluoroalkoxy, $C_1$–$C_4$-alkylthio, trifluoromethylthio or $C_1$–$C_4$-alkoxy-carbonyl), $R^4$ and/or $R^5$ additionally represent phenyl or phenoxy, or represent $C_1$–$C_4$-alkylcarbonylamino, $C_1$–$C_4$-alkoxycarbonylamino, $C_1$–$C_4$-alkylaminocarbonyl-amino or di-($C_1$–$C_4$-alkyl)-amincarbonylamino, or represent the radical —CO—$R^8$, where $R^8$ represents hydrogen,-$C_1$–$C_6$-alkyl, $C_3$–$C_6$-cycloalkyl, $C_1$–$C_6$-alkoxy, $C_3$–$C_6$-cycloalkoxy, $C_3$–$C_6$-alkenyloxy, $C_1$–$C_4$-alkylthio, $C_1$–$C_4$-alkylamino, $C_1$–$C_4$-alkoxyamino, $C_1$–$C_4$-alkoxy-$C_1$–$C_4$-alkyl-amino or di-($C_1$–$C_4$-alkyl)-amino (which are optionally substituted by fluoro and/or chloro), $R^4$ and/or $R^5$ additionally represent trimethylsilyl, $C_1$–$C_4$-alkylsulphonyloxy or di-($C_1$–$C_4$-alkyl)-aminosulphonylamino or represent the radical —CH=N—$R^9$, where $R^9$ represents optionally fluoro-, chloro-, cyano-, carboxyl-, $C_1$–$C_4$-alkoxy-, $C_1$–$C_4$-alkylthio-, $C_1$–$C_4$-alkylsulphinyl- or $C_1$–$C_4$-alkylsulphonyl-substituted $C_1$–$C_6$-alkyl, or represents optionally fluoro- or chloro-substituted benzyl, or represents optionally fluoro- or chloro-substituted $C_3$–$C_6$-alkenyl or $C_3$–$C_6$-alkinyl, or represents optionally fluoro-, chloro-, bromo-, $C_1$–$C_4$-alkyl-, $C_1$–$C_4$-alkoxy-, trifluoromethyl-, trifluoromethoxy- or trifluoromethylthio-substituted phenyl, or represents optionally fluoro- and/or chloro-substituted $C_1$–$C_6$-alkoxy, $C_3$–$C_6$-alkenyloxy, $C_3$–$C_6$-alkinyloxy or benzyloxy, or represents amino, $C_1$–$C_4$-alkylamino, di-($C_1$–$C_4$-alkyl)-amino, phenylamino, $C_1$–$C_4$-alkyl-carbonylamino, $C_1$–$C_4$-alkoxycarbonylamino or $C_1$–$C_4$-alkyl-sulphonylamino or represents optionally fluoro-, chloro-, bromo- or methyl-substituted phenylsulphonylamino, and also $R^3$ represents the radical

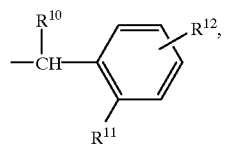

in which $R^{10}$ represents hydrogen or $C_1$–$C_4$-alkyl, $R^{11}$ and $R^{12}$ are identical or different and represent hydrogen, fluoro, chloro, bromo, mtro, cyano, $C_1$–$C_4$-alkyl (which is optionally substituted by fluoro and/or chloro), $C_1$–$C_4$-alkoxy (which is optionally substituted by fluoro and/or chloro), carboxyl, $C_1$–$C_4$-alkoxy-carbonyl, dimethylaminocarbonyl, $C_1$–$C_4$-alkylsulphonyl or di-($C_1$–$C_4$-alkyl)-aminosulphonyl;

and also $R^3$ represents the radical

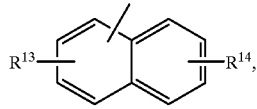

in which $R^{13}$ and $R^{14}$ are identical or different and represent hydrogen, fluoro, chloro, bromo, nitro, cyano, $C_1$–$C_4$-alkyl (which is optionally substituted by fluoro and/or chloro) or $C_1$–$C_4$-alkoxy (which is optionally substituted by fluoro and/or chloro)

or the sodium salt and the potassium, magnesium, calcium, ammonium, $C_1$–$C_4$-alkyl-ammonium, di-($C_1$–$C_4$-alkyl)-ammonium, tri-($C_1$–$C_4$-alkyl)-ammonium, tetra-($C_1$–$C_4$-alkyl)-ammonium, tri-($C_1$–$C_4$-alkyl)-sulphonium, $C_5$- or $C_6$-cycloalkyl-ammonium and di($C_1$–$C_2$-alkyl)-benzyl-ammonium salt of the compounds of the formula (I).

2. A compound of the formula (I) according to claim 1 wherein $Q^1$ represents oxygen or sulphur, $Q^2$ represents oxygen or sulphur, $R^1$ represents in each case optionally fluoro-, chloro-, cyano-, methoxy- or ethoxy-substituted methyl, ethyl, n- or i-propyl, n-, i-, s- or t-butyl, or represents in each case optionally fluoro-, chloro-, or bromo-substituted propenyl, butenyl, propinyl or butinyl, or represents methoxy, ethoxy, n- or i-propoxy or represents allyloxy, or represents methylamino, ethylamino, n- or i-propylamino, n-, i-, s- or t-butylamino, dimethylamino or diethylamino, or represents in each case optionally fluoro-, chloro-, bromo-, methyl- or ethyl-substituted cyclopropyl, cyclobutyl, cyclopentyl, cyclohexyl, cyclopropylmethyl, cyclobutylmethyl, cyclopentylmethyl or cyclohexylmethyl, or represents in each case optionally fluoro-, chloro-, bromo-, cyano-, methyl-, tri-fluoromethyl- or methoxy-substituted benzyl or phenyl, $R^2$ represents in each case optionally fluoro- and/or chloro-, methyl- and/or ethyl-substituted oxetanyl, thietanyl, furyl, tetrahydrofuryl, thienyl, tetrahydrothienyl, oxetanylmethyl, thietanylmethyl, furylmethyl, tetrahydrofurylmethyl, thienylmethyl or tetrahydrothienylmethyl, and $R^3$ represents the radical

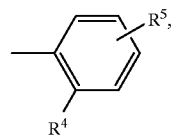

in which $R^4$ represents fluoro, chloro, bromo, methyl, ethyl, n- or i-propyl, trifluoromethyl, methoxy, ethoxy, n- or i-propoxy, n- or i-butoxy, difluoromethoxy, trifluoromethoxy, 2-chloro-ethoxy, 2,2,2-trifluoro-ethoxy, 1,1,2,2-tetrafluoro-ethoxy, 1,1,2,2,2-pentafluoro-ethoxy, 2-methoxy-ethoxy, methylthio, ethylthio, n- or i-propylthio, n- or i-butylthio, 2-fluoro-ethylthio, allyloxy, propargyloxy, methylsulphinyl, ethylsulphinyl, methylsulphonyl, ethylsulphonyl, dimethylaminosulphonyl, diethylaminosulphonyl, N-methoxy-N-methyl-aminosulphonyl, phenyl, phenoxy, methoxycarbonyl, ethoxycarbonyl, n- or i-propoxycarbonyl, and $R^5$ represents hydrogen, fluoro, chloro, bromo methyl, ethyl, n- or i-propyl, trifluoromethyl, methoxy, ethoxy, n- or i-propoxy, difluoromethoxy, trifluoromethoxy, methylthio or ethylthio;

and also $R^3$ represents the radical

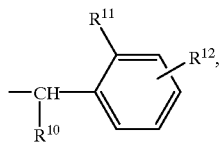

in which $R^{10}$ represents hydrogen, $R^{11}$ represents fluoro, chloro, bromo, methyl, methoxy, difluoromethoxy, trifluoromethoxy, ethoxy, methoxycarbonyl, ethoxycarbonyl, methylsulphonyl or dimethylaminosulphonyl, and $R^{12}$ represents hydrogen.

3. The compound 4-cyclopropyl-5-(3-oxetanyl-oxy)-2-(2-trifluoromethylphenylsulphonylaminocarbonyl)-2,4-dihydro-3H-1,2,4-triazol-3-one.

4. An herbicidal composition comprising an herbicidally effective amount of a compound according to claim 1 and an inert carrier.

5. A method of controlling unwanted vegetation which comprises applying to such vegetation or to a locus from which it is desired to exclude such vegetation an herbicidally effective amount of a compound according to claim 1.

* * * * *